United States Patent [19]
Holliday

[11] Patent Number: 5,657,747
[45] Date of Patent: Aug. 19, 1997

[54] INTERFACE FOR VAPORIZER INTERLOCK

[75] Inventor: Carl Holliday, Hatfield, Pa.

[73] Assignee: N.A.D., Inc., Telford, Pa.

[21] Appl. No.: 635,851

[22] Filed: Apr. 22, 1996

[51] Int. Cl.⁶ .............................. A62B 9/04; A61M 15/00; A61M 16/10; F23D 11/00
[52] U.S. Cl. ............................ 128/202.27; 128/203.12; 128/203.26
[58] Field of Search .................... 128/202.27, 203.12, 128/203.16, 203.17, 203.26, 203.27

[56] References Cited

U.S. PATENT DOCUMENTS

| 3,831,599 | 8/1974 | Needham | 128/203.12 |
| 4,307,718 | 12/1981 | Schreiber. | |
| 4,434,790 | 3/1984 | Olesen | 128/203.12 |
| 4,932,398 | 6/1990 | Lancaster et al. | 128/203.12 |

FOREIGN PATENT DOCUMENTS

| 2070440 | 9/1981 | United Kingdom | 128/203.12 |
| 2193642 | 2/1988 | United Kingdom | 128/203.12 |

Primary Examiner—Kimberly L. Asher
Attorney, Agent, or Firm—Caesar, Rivise, Bernstein, Cohen & Pokotilow, Ltd.

[57] ABSTRACT

A vaporizer interface for use with a vaporizer interlock of an anesthesia apparatus, whereby the vaporizer interlock permits only one vaporizer's contents to be in fluid communication with the anesthesia apparatus at any time, and wherein the vaporizer interface permits the coupling of at least two vaporizers through a rigid rod actuation mechanism to the vaporizer interlock.

9 Claims, 6 Drawing Sheets

INTERFACE FOR VAPORIZER INTERLOCK

FIELD OF THE INVENTION

This invention relates generally to anesthesia apparatus and, more particularly, to interlock devices for anesthesia apparatus vaporizers.

BACKGROUND OF THE INVENTION

Conventional anesthesia apparatus or machines commonly incorporate two separate vaporizers. Each vaporizer is arranged to dispense a metered amount of anesthesia vapor, e.g., Halothane, Enflurane, Methoxyflurane, etc., into the patient breathing circuit, or fresh gas line.

While the construction of commercially available vaporizers varies from manufacturer to manufacturer, the most common type of vaporizer comprises a canister including a reservoir of the anesthesia, valve means and a rotatable dial coupled to the valve means for adjusting the valve means to establish the vaporizer concentration levels. For example, the VAPOR vaporizer used in anesthesia machines sold by N.A.D. Inc., the assignee of the instant invention, includes a rotary dial for adjusting the opening of a valve in the vaporizer to divide the gas flow in the vaporizer in accordance with the dial setting. Part of the gas flow passes through a by-pass, without entering the vaporizer chamber (where the anesthetic is located), while the remaining portion of the gas flow is lead through the vaporizer chamber for saturation by anesthesia vapor. The gas flow which is saturated with the vapor is then combined with the by-pass gas flow so that the whole amount of gas leaves the vaporizer at the set concentration. In the VAPOR vaporizer, the introduction of the gas with the anesthesia vapor into the fresh gas line is effected by an outlet valve under the control of a separate on/off switch. A pair of rotary cams and a pivoting lever are provided to serve as an interlock to insure that the outlet of the vaporizer is opened when the rotary dial is adjusted to any particular setting and to prevent the adjustment dial from being rotated to any setting when the on/off switch is closed, thereby precluding any gas from passing into the vaporization chamber when the outlet of the vaporizer is closed.

In a dual vaporizer anesthesia machine, it is desirable to provide means for preventing both vaporizers from being opened simultaneously since such action prevents an uptake of the vaporizing agent from one vaporizer into the other, which occurrence may have a detrimental effect on the patient. To that end, there is disclosed in U.S. Pat. No. 4,307,718 (Schreiber) a vaporizer exclusion mechanism (hereinafter known as a "vaporizer interlock") to prevent such simultaneous opening. U.S. Pat. No. 4,307,718 (Schreiber) is assigned to the same assignee as the present invention, namely N.A.D., Inc. and whose disclosure is incorporated by reference herein.

In particular, this vaporizer interlock is an interlock device that insures that one vaporizer is closed whenever the other is open and comprises a pair of reciprocable pins and a cooperating pivotable lever. Each pin is arranged to be extended into a cam recess located in a rotary dial on each of the vaporizers (the rotary dial establishes the vapor concentration to be provided) by pivoting action of the lever. Rotation of one dial automatically causes the pin located therein to move out of the cam recess and into contact with the lever. This action pivots the lever and causes it to contact the other pin to extend the other pin into the recess in the associated vaporizer dial, thereby locking the dial closed.

It is therefore desirable to connect any type of vaporizer to the vaporizer interlock disclosed in U.S. Pat. No. 4,307,718 (Schreiber) regardless of the vaporizer configuration.

As shown in FIGS. 1A–1B, there is shown a vaporizer interface 20 that permits the connection of an Ohmeda TEC 6 vaporizer 22 to the vaporizer interlock. As can be seen most clearly in FIGS. 1A and 1B, the TEC 6 vaporizer 22 is directly coupled to the vaporizer interlock L-shaped mounting bracket 46. However, the TEC 6 vaporizer comprises a control knob 24 that does not directly interact with interlock reciprocable pin 54 as disclosed in U.S. Pat. No. 4,307,718 (Schreiber); instead, a series of linkages 26A, 26B and 26C are utilized to couple reciprocable pin 54 movement with the control knob 24 movement. Other than that distinction, operation of the vaporizer interlock with the TEC 6 vaporizer 22 is in accordance with U.S. Pat. No. 4,307,718 (Schreiber): With regard to a common vaporizer interlock and depending on the status of the other vaporizer(s), not shown, the reciprocable pin 54 is either in an extended state (FIG. 1A) or in a retracted state (FIG. 1B). If the reciprocable pin 54 is in the extended state, the internal linkages 26A, 26B and 26C are driven to pivot such that the control knob 24 is "locked-out", thereby preventing the operator from opening the TEC 6 vaporizer 22. (FIG. 1A). On the other hand, if the other vaporizer(s) are in the "locked out" state, the operator can rotate the control knob 24 causing the internal linkages 26A, 26B and 26C to pivot such that the reciprocable pin 54 is retracted, thereby permitting the metered flow of gas from the TEC 6 vaporizer 22.

However, use of the Ohmeda TEC 6 vaporizer 22/interlock interface 20 is restricted to those vaporizers having the same internal construction. For example, the vaporizer interface 20 cannot operate with a DATUM™ vaporizer manufactured by Blease (located in the United Kingdom) which utilizes a vertically-oriented control knob that must be pushed-in before it can be rotated. Therefore, there remains a need for a vaporizer interface that can couple any vaporizer to the vaporizer interlock disclosed in U.S. Pat. No. 4,307,718 (Schreiber).

OBJECTS OF THE INVENTION

Accordingly, it is the general object of this invention to provide a vaporizer interface apparatus which overcomes the disadvantages of the prior art.

It is a further object of this invention to provide a vaporizer interface apparatus for an anesthesia machine which permits various types of vaporizer canisters to be coupled to a vaporizer interlock.

SUMMARY OF THE INVENTION

These and other objects of the instant invention are achieved by providing a vaporizer interface for use on an anesthesia apparatus including a vaporizer interlock. The vaporizer interfacing apparatus operates in conjunction with the vaporizer interlock to mechanically and pneumatically couple at least two vaporizers to the anesthesia apparatus. Each vaporizer is independently selectable and includes an opening mechanism that permits a metered concentration of vapor into a gas flow when opened. The vaporizer interlock comprises at least two reciprocable pins, one pin coupled to the operating mechanism of a respective vaporizer, and a common levering mechanism. A selected vaporizer opening mechanism is operated to drive the common levering mechanism to retract the respective pin of the desired vaporizer, thereby permitting the metered concentration of vapor into the gas flow, while extending all of the other pins to prevent the respective opening mechanisms from opening. The vaporizer interlock also comprises an entry gas conduit and an exit gas conduit. The vaporizer interface comprises an interface block for coupling each of the respective vaporizers to the vaporizer interlock and wherein the interface block further comprises a first gas conduit and a second gas conduit to be in fluid communication with the entry gas conduit and the exit gas conduit, respectively. The vaporizer interface also comprises an actuation means for coupling each of the opening mechanisms to the respective retractable pin. In addition, the vaporizer interface comprises first attachment means for attaching the interface block to the vaporizer to form an assembly. Finally, the vaporizer interface comprises a second attachment means for attaching the assembly to the vaporizer interlock.

DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENT OF THE INVENTION

Figure 1A:
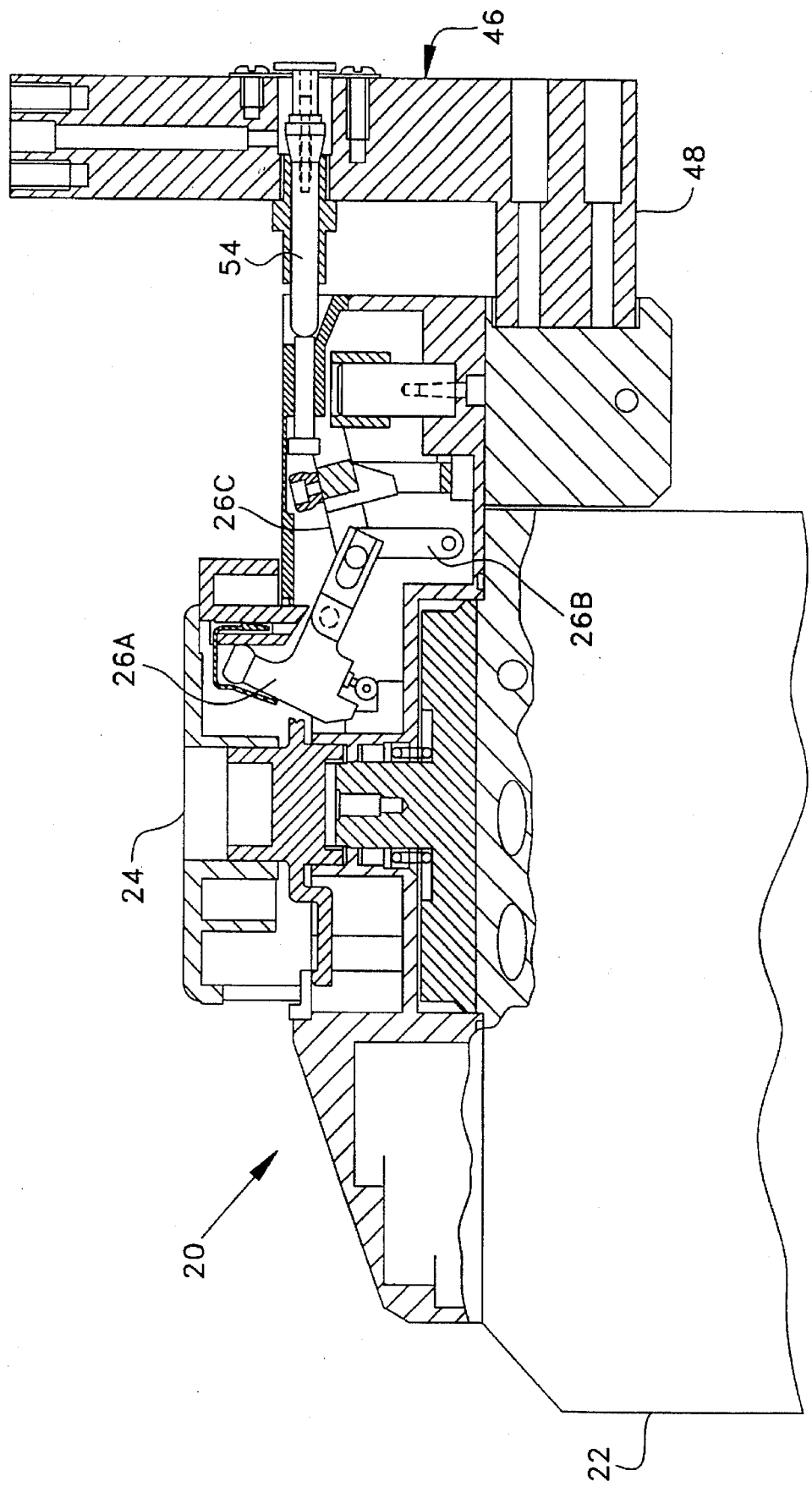
FIG. 1A is a partially-sectioned side view of a Prior Art Ohmeda TEC 6 vaporizer which includes an interface for coupling the vaporizer to a vaporizer interlock and showing the vaporizer in an open condition.
Figure 1B:
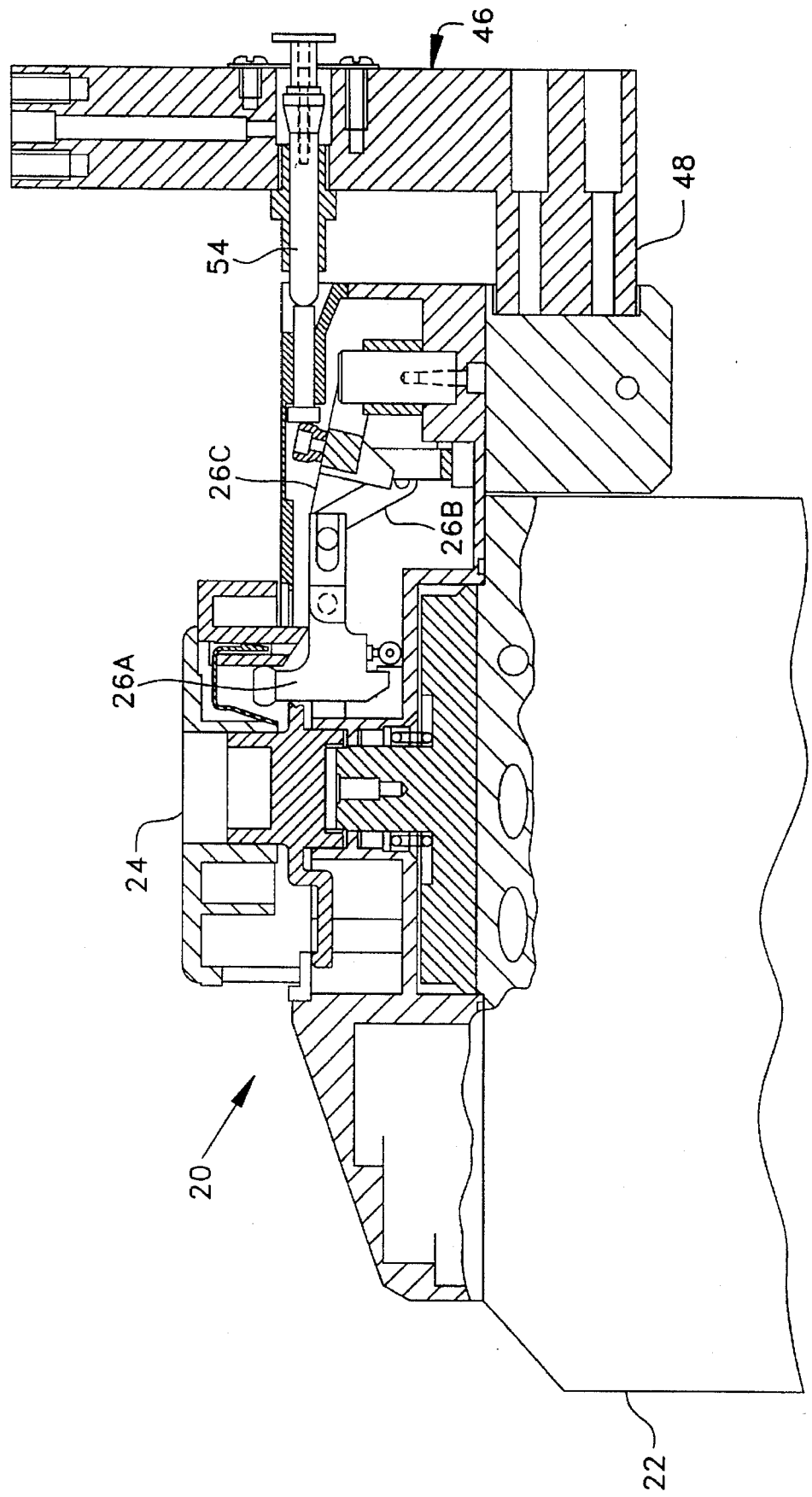
FIG. 1B is a partially-sectioned side view of the Prior Art Ohmeda TEC 6 vaporizer of FIG. 1A but shown in a closed condition.
Figure 2:
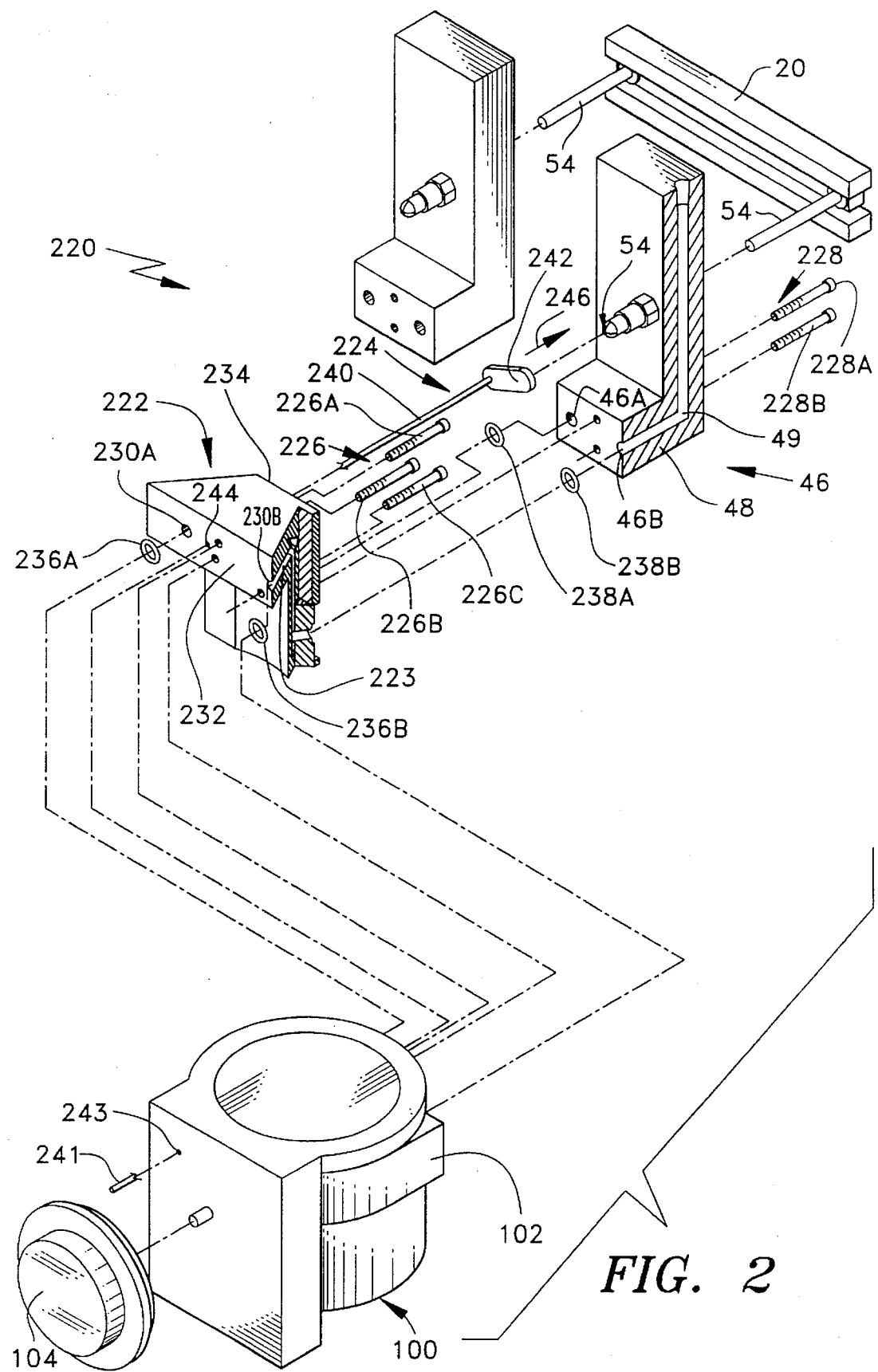
FIG. 2 is a drawing of the present invention shown partially in cross section.

Referring now in greater detail to the various figures of the drawing wherein like reference characters refer to like parts, there is shown generally at 220 in FIG. 2 an interface for coupling a vaporizer 100 (e.g., a DATUM™ vaporizer manufactured by Blease located in the United Kingdom) to the vaporizer interlock 20 of U.S. Pat. No. 4,307,718 (Schreiber). The interface 220 basically comprises an interface block 222, an actuation means 224 and first 226 and second 228 attachment means. As shown in FIG. 2, the first attachment means 226 releasably secures the interface block 222 to the vaporizer 100 and the second attachment means 228 releasably secures the vaporizer 100/interface block 222 assembly to the L-shaped mounting bracket 46.

Figure 3:
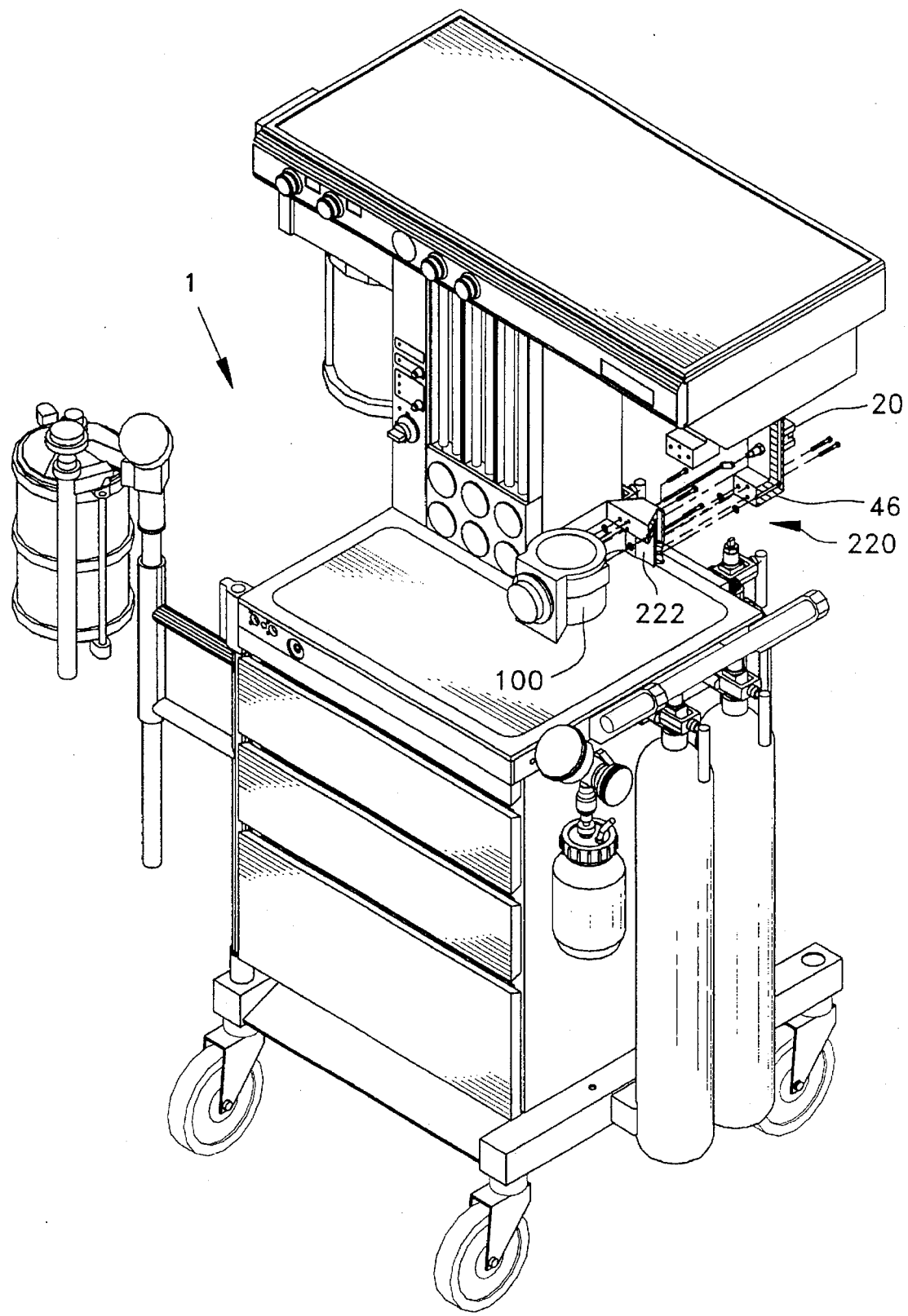
FIG. 3 is an isometric of the present invention, shown partially in cross section, coupled to an anesthesia apparatus.

FIG. 3 depicts how the present invention 220 is coupled to an anesthesia apparatus 1.

Figure 4:
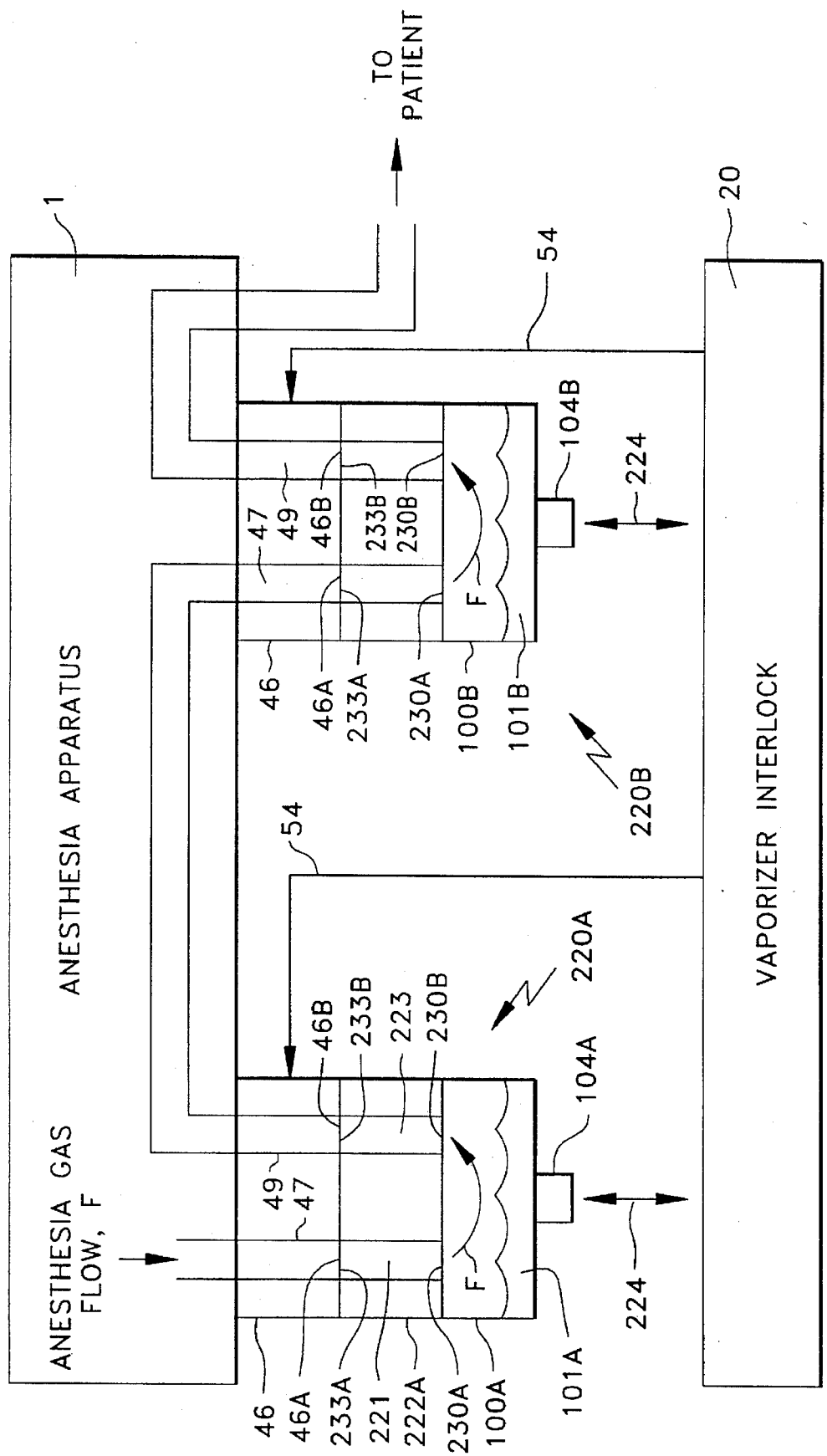
FIG. 4 is an interface diagram of the present invention.

Before a detailed description of the interface 220 is presented, an overview of the vaporizer interface 220 operation is necessary. As shown most clearly in FIG. 4, two vaporizers 100A and 100B are coupled to an anesthesia apparatus 1 via their respective vaporizer interfaces 220A and 220B. Each L-shaped mounting block 46 comprises an entry gas conduit 47 and an exit gas conduit 49 that are in fluid communication with a first gas conduit 221 and a second gas conduit 223, respectively. The exit gas conduit 49 of one L-shaped mounting block 46 is in fluid communication with the entry gas conduit 47 of the immediately adjacent L-shaped mounting block 46, thereby linking the overall anesthesia gas flow, F, in a series configuration. Thus, the anesthesia gas flow F originates in the anesthesia apparatus 1 and flows through each vaporizer interface 220A and 220B and then ultimately to the patient.

Figure 5:
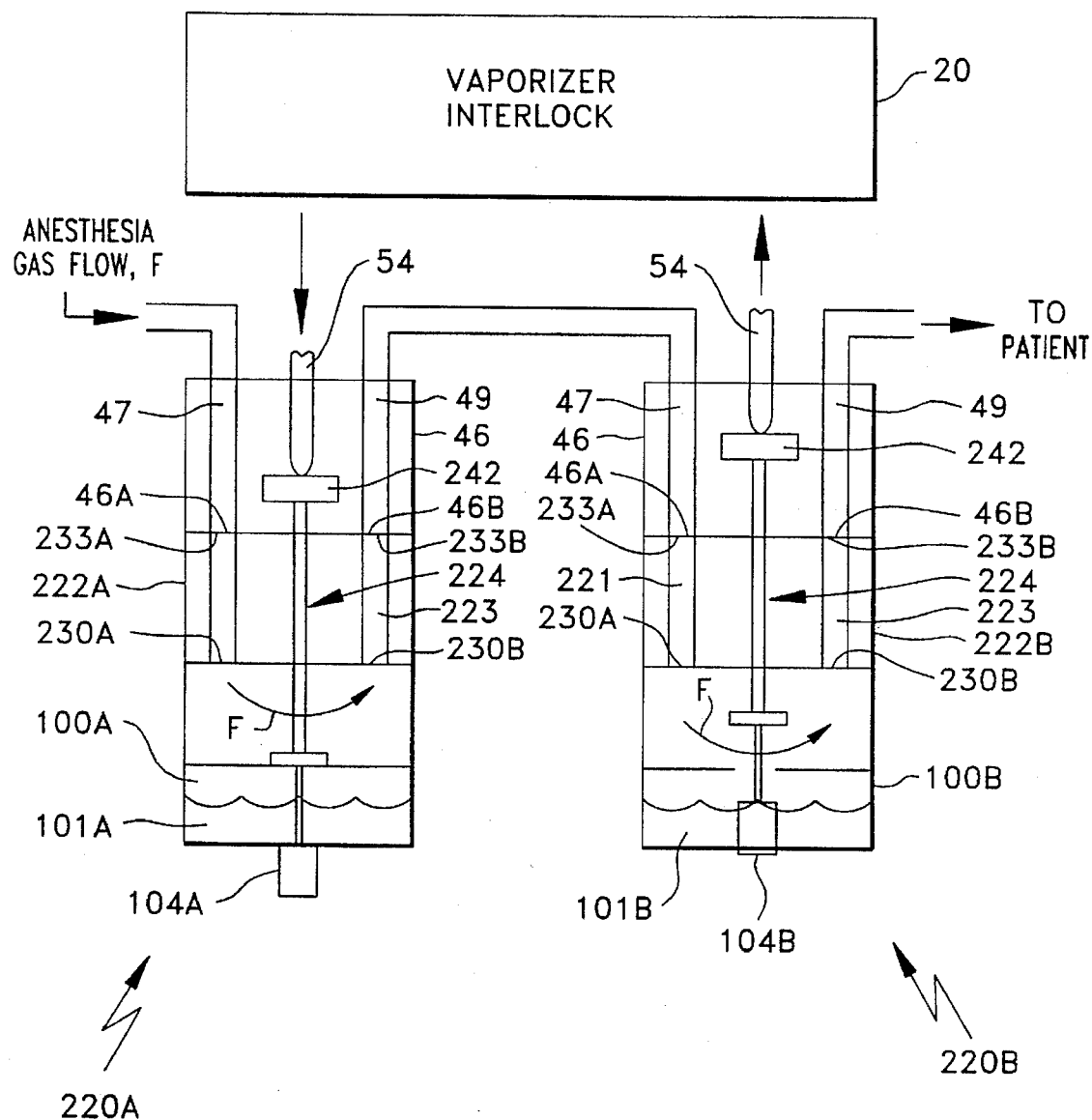
FIG. 5 is a functional diagram of the present invention.

It should be understood that although the gas flow F is through every vaporizer interface 220A and 220B, only the contents (101A and 101B) of one vaporizer 100A or 100B is permitted to enter the gas flow F depending on which vaporizer 100A or 100B is opened by the vaporizer interlock 20. As will be discussed in detail later, when the operator turns a control knob 104 of the vaporizer he/she wants activated, the vaporizer interlock 20 immediately locks out the contents of the remaining vaporizer by positioning the respective pin 54 appropriately, but does not interrupt the gas flow F through the vaporizer interface of the "locked out" vaporizer. This can be most easily seen by the functional diagram of FIG. 5 where vaporizer 100A is "locked out" whereas vaporizer B is open.

The interface block 222 comprises an inverted L-shaped member containing two internal gas conduits 221 (FIGS. 4 and 5) and 223 (FIGS. 2 and 4–5) for the entry and exit of metered gas flow between the vaporizer 100 and the L-shaped mounting bracket 46. Gas conduit ports 230A and 230B, located in an upper portion 232 of the interface block 222, are fluid communication with corresponding ports (not shown) on a corresponding vaporizer portion 102 when the interface block 222 and the vaporizer 100 are releasably secured to each other by the first securement means 226 (e.g., three threaded screws 226A, 226B and 226C). In addition, the back side 234 of the interface block 222 comprises another pair of gas conduit ports 233A and 233B (FIGS. 4 and 5) associated with gas conduit ports 230A and 230B, that are in fluid communication with gas conduit ports 46A and 46B on the lower portion 48 of the L-shaped mounting bracket 46 when the interface block 222/vaporizer 100 assembly are releasably secured to the bracket 46 by the second securement means 228 (e.g., a pair of threaded screws 228A and 228B). Together, the first attachment means 226 and the second attachment means 228 form an anesthesia apparatus-mounting configuration that is field accessible.

As can also be seen in FIG. 2, two pairs of O-rings, 236A/236B and 238A/238B, are disposed between the corresponding gas conduit ports to provide a leakproof-seal when all of the parts are releasably secured to one another. Furthermore, these O-rings comprise material that is compatible with the anesthetic agents used in the anesthesia apparatus 1.

The actuation means 224 permits activation of the vaporizer interlock 20 whenever the control knob 104 on the vaporizer 100 is turned. In particular, the actuation means 224 comprises a push rod 240 having an offset member 242 that transfers the linear in/out motion of the push rod 240 to the reciprocable pin 54 of the vaporizer interlock 20. The push rod 240 is disposed within a channel 244 in the interface block 222 that permits the in/out motion of the rod 240. The other end 241 of the push rod 240 passes through an opening 243 in the vaporizer 100 and is in contact with the control knob 104 (see FIG. 2). Both the push rod 240 and the offset member 242 are fixed with respect to each other, i.e., there is no relative motion between push rod 240 and the offset member 242 during actuation.

When the operator wishes to control the metered flow of the vaporizer 100, the operator pushes the control knob 104. The pushing action drives the push rod 104 inward (arrow 246), thereby causing the offset member 242 to depress the reciprocable pin 54 and thereby permit gas flow in accordance with U.S. Pat. No. 4,307,718 (Schreiber). The operator can then rotate the knob 104 to set the desired level of metered gas flow from the vaporizer 100.

It should be noted that the pushing action of the control knob 104 will only be permitted when the other vaporizers (FIGS. 4 and 5) are prevented from being opened by the interlock. That is, if one of the other vaporizers is opened, the operator will not be able to push the control knob 104 inward because the vaporizer interlock prevents the reciprocable pin 54 from being depressed.

In contradistinction to the TEC 6 vaporizer interface 20, the interface 220 using the actuation means 224 requires no pivoting linkages to transfer movement of the reciprocable pin 54 to the control knob 104. It should also be noted that the actuation means 224 does not necessarily require an offset member 242 to transfer push rod 240 movement; where the internal vaporizer structure 100 permits the push rod 240 to be aligned with the reciprocable pin 54, there is no need for the offset member 242. On the other hand, where clearance problems (internal to the particular vaporizer 100) exist, the position of the channel 244 may not be aligned with the reciprocable pin 54. In that case, the offset member 244 needs to be included on the push rod 240.

It should be further noted that the gas conduits 221 and 223 of the interface block 222 are machined into the block 222. This type of integrated conduit provides a robust and leak free system which assures long term reliability.

Without further elaboration, the foregoing will so fully illustrate my invention that others may, by applying current or future knowledge, readily adopt the same for use under various conditions of service.

I claim:

1. A vaporizer interface for use on an anesthesia apparatus including a vaporizer interlock, said vaporizer interface operating in conjunction with the vaporizer interlock to mechanically and pneumatically couple at least two vaporizers to the anesthesia apparatus, each vaporizer being independently selectable and including an opening mechanism that permits a metered concentration of vapor into a gas flow when opened, the vaporizer interlock comprising at least two reciprocable pins, one pin coupled to the operating mechanism of a respective vaporizer, and a common levering mechanism, a selected vaporizer opening mechanism being operated to drive the common levering mechanism to retract the respective pin of the desired vaporizer, thereby permitting the metered concentration of vapor into the gas flow, while extending all of the other pins to prevent the respective opening mechanisms from opening, the vaporizer interlock also comprising an entry gas conduit and an exit gas conduit, said vaporizer interface comprising:

(a) an interface block for coupling each of the respective vaporizers to the vaporizer interlock, said interface block comprising a first gas conduit and a second gas conduit to be in fluid communication with the entry gas conduit and the exit gas conduit, respectively;

(b) actuation means, disposed within said interface block, for coupling each of the opening mechanisms to the respective retractable pin, said actuation means being movable as a unit with respect to said interface block but with no portion of said actuation means being movable relative to another portion thereof;

(c) first attachment means for attaching said interface block to said vaporizer to form an assembly; and (d) second attachment means for attaching said assembly to the vaporizer interlock.

2. The vaporizer interface of claim 1 wherein said actuation means comprises a rod.

3. The vaporizer interface of claim 2 wherein said actuation means further comprises an offset member.

4. The vaporizer interface of claim 1 wherein said each of said first and second gas conduits is integral with said interface block.

5. The vaporizer interface of claim 1 wherein said first attachment means comprises a plurality of screws that pass through said interface block into the vaporizer to form said assembly.

6. The vaporizer interface of claim 5 wherein said second attachment means comprises a plurality of screws that secure said assembly to the vaporizer interlock.

7. The vaporizer interface of claim 6 wherein said vaporizer interface is field accessible.

8. The vaporizer interface of claim 1 wherein said gas conduits comprise ports, said interface block further comprising O-rings located around every port.

9. The vaporizer interface of claim 8 wherein each of said O-rings is compatible with any anesthetic agent used with the anesthesia apparatus.

* * * * *